(12) United States Patent
Foley et al.

(10) Patent No.: US 6,265,578 B1
(45) Date of Patent: Jul. 24, 2001

(54) PYRIMIDINE-2,4,6-TRIONES

(75) Inventors: Louise Helen Foley, Clifton, NJ (US); Robert Edward Palermo, New York, NY (US); Ping Wang, Nutley, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/483,858

(22) Filed: Jan. 17, 2000

Related U.S. Application Data

(60) Provisional application No. 60/119,903, filed on Feb. 12, 1999.

(51) Int. Cl.[7] .................................................. C07D 239/62
(52) U.S. Cl. ............................................. 544/302; 544/305
(58) Field of Search ...................................... 544/302, 305

(56) References Cited

FOREIGN PATENT DOCUMENTS

| WO 97/23465 | 7/1997 | (WO) . |
| WO 98/58915 | 12/1998 | (WO) . |
| WO 98/58925 | 12/1998 | (WO) . |
| WO98/58925 * | 12/1998 | (WO) . |

OTHER PUBLICATIONS

Welch, A.R., et al., Arch. Biochem. Biophys. 1995, vol. 324, No. 1, Dec. 1, pp. 59–64.

* cited by examiner

Primary Examiner—John M. Ford

(74) Attorney, Agent, or Firm—George W. Johnston; Patricia S. Rocha-Tramaloni; Robert A. Silverman

(57) ABSTRACT

A compound of formula I

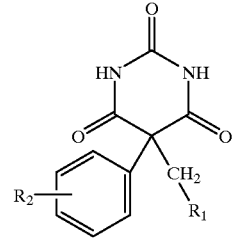

wherein $R_1$ is hydrogen, alkyl, substituted alkyl, alkenyl, substituted alkenyl, alkynyl, substituted alkynyl, alkoxy, substituted alkoxy, aryloxy or alkylalkoxy, and $R_2$ is aryloxy, or a pharmaceutically acceptable salt of an acidic compound of formula I, or a prodrug thereof. The compounds of formula I and their aforementioned salts and prodrugs can be used in the treatment or control of cancer associated with overexpresison of gelatinase-A and/or gelatinase-B, particularly skin cancer, breast cancer, prostate cancer, colon cancer, lung cancer, and gastric cancer. The compounds of the invention are also useful for other diseases associated with unregulated degradation of extracellular matrix, including rheumatoid arthritis, osteoarthritis, multiple sclerosis, corneal ulceration, periodontal disease and the like.

12 Claims, No Drawings

PYRIMIDINE-2,4,6-TRIONES

PYRIMIDINE-2,4,6-TRIONES

This application claims priority under 35 U.S.C. § 119(e) of provisional application Ser. No. 60/119,903, filed Feb. 12, 1999.

BRIEF SUMMARY OF THE INVENTION

The invention relates to compounds of formula I

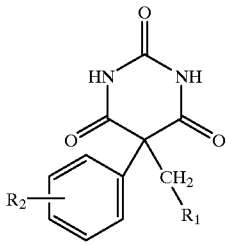

wherein

R$_1$ is hydrogen, alkyl, substituted alkyl, alkenyl, substituted alkenyl, alkyl, substituted alkynyl, alkoxy, substituted alkoxy, aryloxy or alkylalkoxy, and R$_2$ is aryloxy, or a pharmaceutically acceptable salt of an acidic compound of formula I, or a prodrug thereof.

The compounds of the invention are matrix metalloprotease inhibitors useful for treating or controlling cancer associated with overexpression of gelatinase-A and/or gelatinase-B, particularly skin cancer, breast cancer, prostate cancer, colon cancer, lung cancer, and gastric cancer. The compounds of the invention are also useful for other diseases associated with unregulated degradation of extracellular matrix, including rheumatoid arthritis, osteoarthritis, multiple sclerosis, corneal ulceration, periodontal disease and the like.

DETAILED DESCRIPTION OF THE INVENTION

The invention relates to compounds of formula I

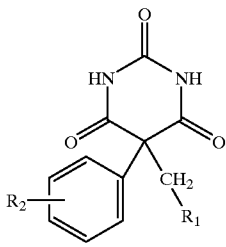

wherein

R$_1$ is hydrogen, alkyl, substituted alkyl, alkenyl, substituted alkenyl, alkynyl, substituted alkynyl, alkoxy, substituted alkoxy, aryloxy or alkylalkoxy, and R$_2$ is aryloxy, or a pharmaceutically acceptable salt of an acidic compound of formula I, or a prodrug thereof.

A prodrug is a compound that may be converted under physiological conditions to a compound of formula I or a pharmaceutically acceptable salt thereof. Preferably, a prodrug is an acyl or alkylmethyl ether derivative of a compound of formula I or a pharmaceutically acceptable salt thereof.

As used herein, the term "alkyl" means a straight or branched-chain alkyl group containing a maximum of 13, preferably a maximum of 7, carbon atoms, such as methyl, ethyl, propyl, isopropyl, butyl, sec-butyl, t-butyl, and pentyl, hexyl and the like.

The term "substituted alkyl" means alkyl which is substituted by one or more substituents, examples of which are hydroxy, halogen, and aryl.

The term "alkenyl" means a straight or branched chain hydrocarbon group containing a maximum of 13, preferably a maximum of 7, and at least 2, carbon atoms, and at least one double bond, such as ethenyl, propenyl, butenyl, pentenyl, hexenyl and the like.

The term "substituted alkenyl" means alkenyl which is substituted by one or more substituents, examples of which are hydroxy, halogen, and aryl.

The term "alkynyl" means a straight or branched chain hydrocarbon group containing a maximum of 13, preferably a maximum of 7, and at least 2, carbon atoms, and at least one triple bond.

The term "substituted alkynyl" means alkynyl which is substituted by one or more substituents, examples of which are hydroxy, halogen, and aryl.

The term "alkoxy" means a straight straight or branched-chain alkoxy group containing a maximum of 11, preferably a maximum of 5, carbon atoms, such as methoxy, ethoxy, propoxy, isopropoxy, butoxy, t-butoxy and the like.

The term "substituted alkoxy" means alkoxy which is substituted by one or more substituents, examples of which are hydroxy, halogen and aryl.

The term alkylalkoxy means a combination of an alkyl or substituted alkyl group and an alkoxy or substituted alkoxy group.

The term "aryl", alone or in combination, means an aromatic carbocyclic ring or a heterocyclic ring, which is unsubstituted or substituted by one or more, preferably one to three, substituents, examples of which are alkyl, hydroxy, alkoxy, and halogen. Examples of aromatic carbocyclic rings are phenyl and naphthyl. Examples of aromatic heterocyclic rings are pyridino, pyrrolo, thienyl, pyrazolo, imidazolo, thiazolo, oxazolo, triazolo, tetrazolo, oxadiazolo, thiadiazolo, benzofuryl, benzothienyl, benzimidazolo, benzotriazolo, quinolinyl, isoquinolinyl, and indolyl. Most preferably, aryl is an unsubstituted phenyl group or phenyl group having one or more, preferably one to three, substituents, examples of which are halogen, alkyl, hydroxy, alkoxy, and halogen.

The term "halogen" means fluorine, chlorine, bromine, or iodine.

The term "acyl" means a group derived from an alkanoic acid, for example, acetyl, propionyl or butyryl, or from an aromatic carboxylic acid for example, benzoyl. Examples of substituents on alkanoic acid includes one or more of the following: hydroxy, alkoxy, amino, halogen, thioalkyl, carboxy, carboxylic acid derivative or alkyl sulphinyl and the like. Examples of substituents on aromatic carboxylic acid include one or more of the following: halogen, alkyl, hydroxy, benzyloxy, alkoxy, haloalkyl, nitro, amino, cyano and the like.

Preferably, R$_1$ is hydrogen, alkyl, substituted alkyl, or substituted alkoxy. More preferably, R$_1$ is hydrogen, alkyl containing a maximum of 7 carbon atoms, substituted alkyl containing a maximum of 7 carbon atoms (preferably hydroxymethyl) or substituted alkoxy containing a maximum of 5 carbon atoms (preferably benzyloxy).

Preferably, R$_2$ is in the para position. More preferably, R$_2$ is phenoxy.

Preferably, the compound of formula I is 5-methyl-5-(4-phenoxyphenyl) pyrimidine-2,4,6-trione, 5-hexyl-5-(4-phenoxyphenyl)pyrimidine-2,4,6-trione, 5-benzyloxymethyl-5-(4-phenoxyphenyl)pyrimidine-2,4,6-trione, or 5-(2-hydroxyethyl)-5-(4-phenoxyphenyl) pyrimidine-2,4,6-trione.

The compounds of formula I may be prepared by the following Schemes I–II.

The compounds of formula I are prepared by the following Scheme I.

SCHEME I

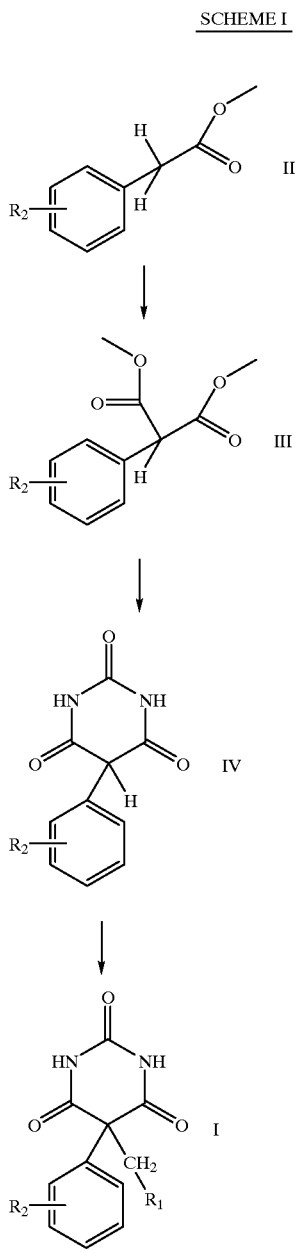

Compounds of formula III are prepared by treatment of compounds of formula II with a strong base, such as sodium hydride, lithium diisopropylamide, or lithium bis (trimethylsilyl)amide, in an aprotic solvent such as tetrahydrofuran (THF). The resultant anion is then reacted with with dimethylcarbonate or methyl chloroformate at temperatures ranging from room temperature to reflux to form a compound of formula III.

The compounds of formula IV are prepared by reacting a compound of formula III with urea in a basic solution, such as sodium methoxide in methanol, at reflux.

The compounds of formula I are prepared by reacting a compound of formula IV with a strong base, such as sodium hydride, lithium diisopropylamide, lithium bis (trimethylsilyl)amide, in an aprotic solvent, such as THF, to form an anion. The anion is then treated with alkyl halide, such as methyl iodide, hexyl bromide, allyl bromide, or benzyl chloromethyl ether, at temperatures varying from room temperature to reflux. N-substituted-2,4,6-triones are then removed by chromatography to provide the desired compound of formula I.

The compounds of formula II are known or can prepared by known methods.

The compounds of formula I can also be prepared as described in Scheme II.

SCHEME II

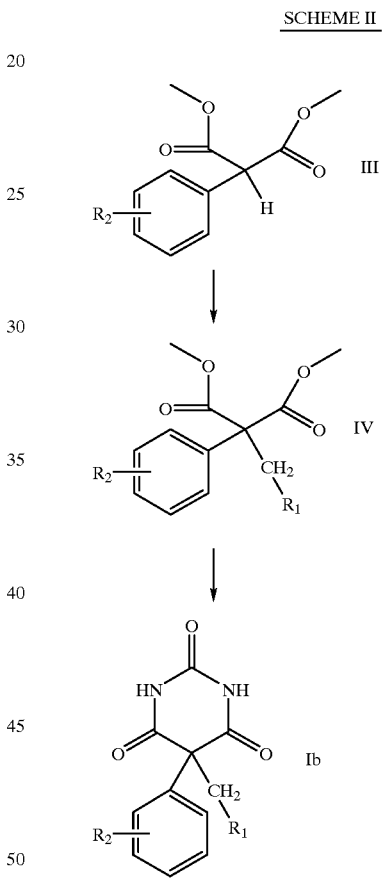

Compounds of formula V are prepared by reacting a compound formula III with a strong base such as sodium hydride, lithium diisopropylamide, lithium bis(trimethylsilyl)amide, in an aprotic solvent such as THF. The resulting anion is then treated with an alkyl halide, such as methyl iodide, hexyl bromide, allyl bromide, or benzyl chloromethyl ether, at temperatures varying from room temperature to reflux.

In the case of a compound of formula V wherein $R_1$ is hydroxymethyl, compounds of formula V are also prepared by reacting a compound formula III with a strong base such as sodium hydride, lithium diisopropylamide, lithium bis (trimethyl-silyl)amide, in an aprotic solvent such as THF. The resulting anion is then treated with ethylene oxide. Alternatively, in the case of a compound of formula V wherein $R_1$ is hydroxymethyl, compounds of formula V are also prepared by carrying out oxidative cleavage of the compound of formula III, dimethyl 2-(2-propenyl)-2-(4-phenoxy-phenyl)malonate, with ozone and reducing the resultant ozonide with a phosphine or a thiol to give the aldehyde which is then reduced to the alcohol, using a reducing agent such as sodium borohydride.

Compounds of formula I are prepared by heating compounds of formula V with urea in the presence of $Mg(OCH_3)_2$ as a paste at 80–100° C. for a period of time necessary to complete the reaction.

If desired, an acidic compound of formula I can be converted into a pharmaceutically acceptable salt with a base in a known manner. Suitable salts are those derived not only from inorganic bases, for example, sodium, potassium or calcium salts, but also from organic bases such as ethylenediamine, monoethanolamine or diethanolamine.

Prodrugs are made, for example, by reacting activated acids with a compound of formula I by known methods, or by reacting halomethylalkyl ether with a compound of formula I by known methods.

The compounds of formula I and their pharmaceutically acceptable salts and prodrugs inhibit matrix metalloprotease and so are useful for treating or controlling cancer associated with overexpresison of gelatinase-A and/or gelatinase-B, particularly skin cancer, breast cancer, prostate cancer, colon cancer, lung cancer, and gastric cancer. The compounds of the invention are also useful for other diseases associated with unregulated degradation of extracellular matrix, including rheumatoid arthritis, osteoarthritis, multiple sclerosis, corneal ulceration, periodontal disease and the like.

Human 72 kDa gelatinase was purified from the conditioned media of fetal lung fibroblasts according to known methods. The enzyme was stored in the pro-form at −80° C. and activated prior to use by treatment with 1 mM aminophenyl mercuriacetate (APMA) for 1 hour at 37° C., then dialyzed against reaction buffer before use. Human neutrophil gelatinase (95 kDa gelatinase) was purified from conditioned media of NSO-cells according to known methods. This enzyme was likewise stored in the zymogen form at −80° C. It was activated by treatment with trypsin (5 µg/mL) for 1 hour at 37° C., followed by addition of bovine pancreatic trypsin inhibitor to 50 µg/mL. Human matrilysin was obtained from a bacterial expression system as a ubiquitin fusion construct Welch, A. R., Holman, C. M., Browner, M. F., Gehring, M. R., Kan, C.-C., & Van Wart, H. E. (1995) *Arch. Biochem. Biophys.* 324, 59–64. The mature form of matrilysin was purified following activation with 1 mM APMA (1 hour, 37° C.) and the active enzyme stored at −80° C. The catalytic domain of human collagenase-3 was obtained in a manner analogous to that for matrilysin. The final form of collagenase-3 used for these studies consisted of the residues $Tyr_{104}$–$Asn_{274}$ from the full length collagenase sequence. The catalytic domain of human stromelysin-1 was produced via *E. coli* expression and purification according to known methods; the activated, catalytic domain was stored at −80° C.

The assay methods utilized the fluorogenic substrate: Dnp-Pro-Cha-Gly-Cys(Me)-His-Ala-Lys(NMA)-$NH_2$. (Dnp=dinitro phenyl; Cha=cyclohexylalanine; Cys(Me)=S-methyl cysteine, Lys(NMA)=$N^\epsilon$-methyl-anthranoyl-1-lysine). Stock solutions were prepared in DMSO. Stock solutions of compounds of formula I (inhibitor) were also prepared in DMSO. All reactions had a net final DMSO level of 5% (v/v) in the indicated buffers for the enzymes.

For gelatinase-A and gelatinase-B, the buffer was pH 7.5, 50 mM TrisHCl, 200 mM NaCl, 5 mM $CaCl_2$, 20 µM $ZnCl_2$, 0.05% (wt/v) Brij-35. For matrilysin and the catalytic domain of collagenase-3, the buffer composition was pH 7.5, 50 mM Hepes, 200 mM NaCl, 5 mM $CaCl_2$, 20 µM $ZnCl_2$, 0.05% (wt/v) Brij-35. The final substrate concentration in all cases 10 µM. The approximate concentrations for the enzymes were: gelatinase-A, 0.8 nM; gelatinase-B, 0.5 nM; collagenase-3, 0.4 nM; matrilysin, 10 nM. To perform the peptide cleavage assay, the vessel containing buffer and compound of formula I were pre-equilibrated at 37° C., then the reaction initiated by successive addition of concentrated stocks of enzyme and substrate, and incubation at 37° C. was continued. At successive time points between 30 and 120 minutes, 50 µL aliquots of the assays were pulled and the enzymatic reaction stopped by addition to 150 µL of 30 mM EDTA (pH 7.4) in the well of a black, flat bottom microtiter plate. The extent of substrate conversion was determined by reading the fluorescence of the stopped reactions (excitation wavelength: 355 nm; emission wavelength: 460 nM). Positive controls were run in the absence of inhibitor; negative controls had no enzyme and showed negligible spontaneous cleavage.

Plots of the fluorescence vs time (30–120 min) were linear; comparison to standards showed the substrate conversion was <20% in all instances. A rate at each inhibitor concentration was obtained from a linear least squares fit to the fluorescence time course. The percent inhibition at inhibitor concentration [I] was calculated as:

$$\% \text{ inh}[I]=100(1-\text{rate}[I]/\text{ratePC})$$

where

%inh[I]=percent inhibition at inhibitor concentration [I]
rate[I]=rate at inhibitor concentration [I]
ratePC=rate of positive control The $IC_{50}$ for the inhibitor was then obtained by fitting the concentration dependence of the %inh[I] to the simple binding isotherm:

$$\% \text{ inh}[I]=100(([I]/(IC_{50}+[I]))$$

Measurements for stromelysin-1: the catalytic domain of stromelysin-1 was tested using the same substrate but with a modified protocol. The assay buffer was pH 6.5 50 mM Mes, 2.5 mM EDTA, 5 mM $CaCl_2$, and 0.05% (wt/v) Brij-35. The substrate concentration was 10 µM and the enzyme concentration was 10 nM. Reactions were performed at ambient temperature. Appropriate portions of buffer, substrate, and inhibitor were combined in the well of a black, flat bottom microtiter plate. The reaction was started by addition of an aliquot of enzyme stock and the generated fluorescence was read directly after 60 minutes. Positive controls were run in the absence of inhibitor. Negative controls lacked enzyme and showed a finite increase during the course of the assay; to correct the enzymatic reactions, this background fluorescence was subtracted from the values for the positive control and the inhibited reactions. The %inh[I] was calculated as:

$$\% \text{ inh}[I]=100(1-\text{Fluor}[I]/\text{FluorPC})$$

where Fluor[I]=corrected fluorescence at 60 minutes observed for inhibitor concentration [I]

FluorPC=corrected fluorescence at 60 minutes observed for the positive control

The $IC_{50}$ for the inhibitor was then obtained by fitting the %inh[I] to the single site binding isotherm indicated above.

The $IC_{50}$ are provided in the Table below for compounds of formula I.

| Compound | Strom-1 | Matr | Coll-3 | GelA | GelB |
|---|---|---|---|---|---|
| A | 2 µM | >50 µM | 65 nM | 80 nM | 52 nM |
| B | 2 µM | >50 µM | 78 nM | 67 nM | 50 nM |
| C | 930 nM | >50 µM | 47 nM | 26 nM | 23 nM |
| D | — | — | — | 59 nM | 118 nM |

A=5-methyl-5-(4-phenoxyphenyl)pyrimidine-2,4,6-trione.
B=5-hexyl-5-(4-phenoxyphenyl)pyrimidine-2,4,6-trione.
C=5-benzyloxymethyl-5-(4-phenoxyphenyl)pyrimidine-2,4,6-trione.
D=5-(2-hydroxyethyl)-5-(4-phenoxyphenyl)pyrinidine-2,4,6-trione.

The compounds of formula I and their salts and prodrugs can be used as medicaments, for example, in the form of pharmaceutical prepareations, which can be administered orally, for example, in the form of tablets, coated tablets, dragees, hard or soft gelatin capsules, solutions, emulsions or suspensions. They can also be administered rectally, for example, in the form of suppositories or parenterally, for example in the form of injection solutions.

For the manufacture of pharmaceutical preparations these compounds can be formulated with therapeutically inert, inorganic or organic carriers. Lactose, maize starch or derivatives thereof, talc, stearic acid or its salts can be used as such carriers for tablets, coated tablets, dragees and hard gelatin capsules. Suitable carriers for soft gelatin capsules are vegetable oils, waxes, fats, semi-solid or liquid polyols. Depending on the nature of the active substance no carriers are, however, generally required in the case of soft gelatin capsules. Suitable carriers for the manufacture of solutions and syrups are water, polyols, saccharose, invert sugars, and glucose. Suitable carriers for injection solutions are water, alcohols, polyols, glycerine and vegetable oils. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain still other therapeutically valuable substances.

The compounds of formula I and their aforementioned salts and prodrugs can be used in the treatment or control of cancer associated with overexpresison of gelatinase-A and/or gelatinase-B, particularly skin cancer, breast cancer, prostate cancer, colon cancer, lung cancer, and gastric cancer. The compounds of the invention are also useful for other diseases associated with unregulated degradation of extracellular matrix, including rheumatoid arthritis, osteoarthritis, multiple sclerosis, corneal ulceration, periodontal disease and the like. The dosage can vary within wide limits and will be adjusted to the individual requirements of each particular case. In general, in the case of oral or parenteral administration to adult humans, a daily dosage of about 10 mg to 1000 mg, and preferably 100 mg to 500 mg, should be appropriate, although the upper limit may be exceeded when this is found to be expedient. The daily dose can be administered as a single dose or in divided doses, or for parenteral administration, it may be given as continuous infusion.

The following examples illustrate, without limitation, the present invention.

EXAMPLE 1

To a suspension of NaH (1.02 g of 60% NaH in mineral oil washed with hexanes, 0.61 g, 25.6 mmol) in dry THF (30 mL) was added methyl (4-phenoxyphenyl)acetate (2.7 g, 11.1 mmol) in dry THF (10 mL). The resulting mixture was stirred at room temperature for 30 minutes and then dimethylcarbonate (4.0 g, 3.75 mL, 44.4 mmol) was added . The reaction mixture was heated to reflux overnight and then cooled to room temperature, quenched with 1N HCl (60 mL), and extracted with ether (2×100 mL). The combined organic extracts were washed with water, then brine, dried ($Na_2SO_4$), concentrated, and purified using HPLC (porasil) eluted with 15% EtOAc/hexanes to give 2.56 g of dimethyl 2-(4-phenoxyphenyl)malonate as a white solid: $^1$H NMR (200 mHz, $CDCl_3$) δ 7.39–6.92 (9H, m), 4.65 (1H, s), 3.75 (6H, s).

EXAMPLE 2

To a $NaOCH_3$ solution (prepared by allowing 0.23 g of Na metal to react with 7.2 mL dry $CH_3OH$) was added dimethyl 2-(4-phenoxyphenyl)malonate (1.0 g, 3.33 mmol) followed by urea (0.4 g, 6.66 mmol). The resulting white reaction mixture was refluxed for 24 hours and then cooled to 0° C. and acidified with 3N HCl. The white solids were filtered and washed with water and dried to give 900 mg of crude product. This was further purified by trituration with EtOAc/hexanes (1:1) to afford 5-(4-phenoxyphenyl)pyrimidine-2,4,6-trione as a white powder (830 mg): $^1$H NMR (400 mHz, $CDCl_3$) 3:2 keto/enol form δ 11.38 (2×NH keto form, s), 10.58 (2×NH enol form, s), 7.46–6.91(9H, m), 4.85 (H-5, s); HRMS Calcd for $C_{16}H_{12}N_2O_4$ 296.0796; Found 296.0806.

EXAMPLE 3

Carried out under an inert atmosphere:

To a suspension of NaH (16.21 g of 60% in mineral oil, 9.72 mg, 0.405 mmol) in dry THF was added 5-(4-phenoxyphenyl)pyrimidine-2,4,6-trione (100 mg, 0.34 mmol). After the mixture stirred at room temperature for 30 minutes, methyl iodide (48.2 mg, 0.34 mmol) was added. The reaction was stirred at room temperature for 3 hours and then additional NaH (24 mg of 60% in mineral oil, 14 mg, 0.60 mmol) was added followed by methyl iodide (96.4 mg, 0.86 mmol). This reaction mixture was stirred at room temperature for 2 hours and then refluxed overnight. The reaction solution was diluted with EtOAc and then quenched with 1N HCl. The organic layer was separated washed with water, brine, dried ($Na_2SO_4$), concentrated, and then purified by chromatography on a Chromatotron using a silica gel plate (1000 micron) with 30% EtOAc/ hexanes and then 50% EtOAc/hexanes and fmally EtOAc to afford 1,3-di-N-methyl-5-methyl-5-(4-phenoxyphenyl)pyrimidine-2,4,6-trione (7.3 mg) and 1-N-methyl-5-methyl-5-(4-phenoxyphenyl)pyrimidine-2,4,6-trione (10.0 mg) and then 5-methyl-5-(4-phenoxyphenyl)pyrimidine-2,4,6-trione (27 mg) in order of elution.

Spectra for 5-methyl-5-(4-phenoxyphenyl)pyrimidine-2,4,6-trione: $^1$H NMR (200 mHz, $CD_3OD$) δ 7.37–6.95 (9H, m), 1.77 (3H, s); HRMS Calcd for $C_{17}H_{14}N_2O_4$ 310.0954; Found 310.0963.

Spectra for 1-N-methyl-5-methyl-5-(4-phenoxyphenyl)pyrimidine-2,4,6-trione: $^1$H NMR (200 mHz, $CDCl_3$) δ 8.38 (1NH, s), 7.39–6.92 (9H, m), 3.31 (3H, s), 1.86 (3H, s); HRMS Calcd for $C_{18}H_{16}N_2O_4$ 324.1110; Found 324.1116.

Spectra for 1,3-di-N-methyl-5-methyl-5-(4-phenoxyphenyl)pyrimidine-2,4,6-trione: $^1$H NMR (200 mHz, $CDCl_3$) δ 7.38–6.91(9H, m), 3.34 (6H, s), 1.85 (3H, s); HRMS Calcd for $C_{19}H_{18}N_2O_4$ 338.1267; Found 338.1267.

EXAMPLE 4

Step 1:

Carried out under an inert atmosphere:

To a suspension of NaH (144 mg of 60% in mineral oil washed with hexanes, 86.4 mg, 3.6 mmol) in dry THF (20 mL) was carefully added dimethyl 2-(4-phenoxyphenyl) malonate (900 mg, 3.0 mmol). The resulting mixture was stirred at room temperature for 1 hour and then 1-iodohexane (1.27 g, 0.89 mL, 6.0 mmol) was added. The reaction mixture was stirred at room temperature for 1 hour and then heated to reflux overnight. The reaction was cooled to room temperature and quenched with 1N HCl (20 mL) and extracted with ether (2×40 mL). The combined organic extracts were washed with saturated $Na_2S_2O_3$, water, then brine, dried ($Na_2SO_4$), concentrated, and purified by chromatography using a Chromatotron with a silica gel plate (4000 micron) eluted with 13% EtOAc/hexanes to give 950 mg of dimethyl 2-(4-phenoxyphenyl)-2-n-hexylmalonate as a viscous oil. $^1$H NMR (200 mHz, $CDCl_3$) δ 7.39–6.92 (9H, m), 3.75 (6H, s), 2.10 (2H, t), 1.29 (8H, m), 0.87 (3H, t).

Step 2:

$Mg(OCH_3)_2$ was prepared as follows: To a 25 mL round-bottom flask under argon was added Mg tunings (90 mg, 3.70 mmol), dry $CH_3OH$ (2 mL), 2 drops of $CCl_4$ and a catalytic amount of Mg powder. An exothermic reaction took place and hydrogen gas evolution was observed. After the initial exothermic reaction subsided, the reaction mixture was heated to reflux for 1 hour and then cooled to room temperature. Dimethyl 2-(4-phenoxyphenyl)-2-n-hexylmalonate (500 mg, 1.30 mmol) and urea (162 mg, 2.70 mmol) were added to the $Mg(OCH_3)_2$. The reaction mixture was heated at 85–90° C. for 1 hour and then excess $CH_3OH$ was distilled off until a fluid-paste was obtained and this paste was then heated at 85–90° C. overnight. The reaction was cooled to room temperature, diluted with EtOAc, and washed with 1N HCl. The acidic aqueous layer was re-extracted with EtOAc. The combined EtOAc extracts were washed with water, brine, dried ($MgSO_4$), and concentrated. The resulting oil was purified with HPLC (porasil) using 30% EtOAc/hexanes as eluent to afford 330 mg of 5-n-hexyl-5-(4-phenoxyphenyl)pyrimidine-2,4,6-trione as a white foam: $^1$H NMR (400 mHz DMSO-d6) δ 11.71 (2NH, s), 7.42–6.99 (9H, m), 2.22 (2H, t), 1.24 (8H, m), 0.85 (3H, t); HRMS Calcd for $C_{22}H_{24}N_2O_4$ 380.1736; Found 380.1740.

EXAMPLE 5

Step 1:

Carried out under an inert atmosphere.

To a suspension of NaH (0.37 g of 60% in mineral oil washed with hexanes, 0.22 g, 9.2 mmol) in dry THF (30 mL) was carefully added dimethyl 2-(4-phenoxyphenyl) malonate (2.5 g, 8.33 mmol). The resulting mixture was stirred at room temperature for 30 minutes and then benzyl chloromethyl ether (1.43 g, 1.27 mL, 9.16 mmol) was added. The reaction mixture was stirred at room temperature overnight and quenched with sat. $NH_4Cl$ and then extracted with ether (100 mL). The ether extract was dried ($MgSO_4$), and concentrated to give 4.0 g of viscous oil. This was purified using HPLC (porasil) eluted with 15% EtOAc/hexanes to give 2.1 g of dimethyl 2-benzyloxymethyl-2-(4-phenoxyphenyl)malonate as a viscous oil: $^1$H NMR (200 mHz, $CDCl_3$) δ 7.48–6.95 (14H, m), 4.55 (2H, s), 4.20 (2H, s), 3.75 (6H, s).

Step 2:

$Mg(OCH_3)_2$ was prepared as described in Example 4 Step 2 from: Mg (116 mg, 4.76 mmol), dry $CH_3OH$ (3.0 mL), 1 drop of $CCl_4$, catalytic amount of Mg powder. To this was added dimethyl 2-benzyloxymethyl-2-(4-phenoxyphenyl) malonate (700.0 mg, 1.67 mmol), urea (208.0 mg, 3.47 mmol) and the mixture heated to reflux and then excess $CH_3OH$ distilled off until a paste was obtained. The resulting paste was heated at 85–90° C. overnight. Workup as described in Example 4 gave, after concentration, a viscous oil (0.75 g) which was chromatographed using a Chromatotron with a silica gel plate (4000 micron) and eluted with 40% EtOAc/hexanes to give 180 mg of 5-benzyloxymethyl-5-(4-phenoxyphenyl)pyrimidine-2,4,6trione as a white solid: $^1$H NMR (400 mHz, DMSO-d6) δ 8.01 (2NH, s), 7.38–6.94 (15H, m), 4.58 (2H, s), 4.27 (2H, s); HRMS Calcd for $C_{24}H_{20}N_2O_5$ 416.1372; Found 416.1383.

EXAMPLE 6

Step 1:

A solution of dimethyl 2-(4-phenoxyphenyl)malonate (2.56 g, 8.54 mmol) in dry THF (50 mL) was cooled to –78° C. and then lithium diisopropylamide (4.7 mL of a 2M solution in ThF, 9.8 mmol) was added. The reaction was stirred at –78° C. for 1 hour and then allyl bromide (11.4 mg, 9.4 mmol) was added. The reaction was stirred at –78° C. for 3 hours and then allowed to warm to room temperature and heated in a 75° C. oil bath until the reaction was shown to be complete by TLC. The reaction was cooled to room temperature and quenched with 1N HCl. Extraction with ether and drying of the ether extracts ($MgSO_4$) gave crude product. Purification by filtration through silica gel 60 (70–230 mesh) using EtOAc, followed by HPLC (porasil) using 11% EtOAc/hexanes gave 1.8 g of dimethyl 2-(2-propenyl)-2-(4-phenoxyphenyl)malonate as a viscous oil: $^1$H NMR (200 mHz, $CDCl_3$) δ 7.4–6.85 (9H, m), 5.75 (1H, m), 5.05 (2H, m), 3.75 (6H, s), 3.1 (2H, d).

Step 2:

A solution of dimethyl 2-(2-propenyl)-2-(4-phenoxyphenyl)malonate (1.8 g, 5.3 mmol) in $CH_2Cl_2$ (200 mL) was cooled to –70° C. and then $O_3$ bubbled through until a blue color persisted. The blue solution was degassed with argon and while still at –70° C. was treated with $Ph_3P$ (4.0 g, 15.2 mmol) and allowed to warm slowly to room temperature. Concentration, followed by purification by HPLC (porasil) using 20% EtOAc/hexanes gave 1.66 g of the aldehyde as an oil. This was dissolved in $CH_3OH$ (50 mL) and $NaBH_4$ (0.184 g, 4.85 mmol) was added and the reaction stirred at room temperature 30 minutes. Following concentration, the residue was dissolved in EtOAc and washed with water, brine, and then dried ($MgSO_4$), and concentrated to give 1.55 g of a mixture of dimethyl 2-(2-hydroxyethyl)-2-(4-phenoxyphenyl)malonate and its derived lactone.

Step 3:

$Mg(OCH_3)_2$ was prepared as described in Example 4 Step 2 from: Mg (116 mg, 4.76 mmol), 3 mL of $CH_3OH$, 1 drop of $CCl_4$, and a catalytic amount of Mg powder. To this was added the above mixture of dimethyl 2-(2-hydroxyethyl)-2-(4-phenoxyphenyl)malonate and its derived lactone (521 mg, 1.67 mmol) and urea (228 mg, 3.47 mmol) and the mixture heated to reflux and then excess $CH_3OH$ distilled off until a paste was obtained. The resultant paste was heated at 85–90° C. for 8 hours and then cooled to room temperature. The reaction was partitioned between EtOAc and 10 mL 1N HCl. The EtOAc layer was separated, dried ($Na_2SO_4$), and concentrated to give 600 mg of a crude product Chromatography using a Chromatotron with a silica gel plate (2000 micron) eluted with EtOAc gave 120 mg of pure 5-(2-hydroxyethyl)-5-(4-phenoxy-phenyl)pyrimidine-2,4,6-trione as a white solid: IR (KBr) 3214, 3100, 1765(sh), 1705 cm-1; $^1$H NMR (400 mHz, DMSO-d6) δ 11.48 (2H, br s, N—H), 7.45–6.95 (9H, m), 4.85 (1H, t, OH), 3.50 (2H, m), 2.50 (2H, m); HRMS Calcd for $C_{18}H_{16}N_2O_5$ 340.1059, Found 340.1055.

EXAMPLE 7

| | | Example 7 TABLET FORMULATION | | | | | |
|---|---|---|---|---|---|---|---|
| | | | | mg/Tablet | | | |
| Item | Ingredients | 5 mg | 25 mg | 100 mg | 250 mg | 500 mg | 750 mg |
| | | KERNEL: | | | | | |
| 1 | Compound of formula I | 5.0 | 25.0 | 100.0 | 250.0 | 500.0 | 750.0 |
| 2 | Anhydrous Lactose | 104.4 | 84.4 | 36.8 | 23.5 | 47.0 | 70.5 |
| 3 | Croscarmellose Sodium | 6.0 | 6.0 | 7.5 | 15.0 | 30.0 | 45.0 |
| 4 | Povidone K30 | 3.6 | 3.6 | 4.5 | 9.0 | 18.0 | 27.0 |
| 5 | Magnesium Stearate | 1.0 | 1.0 | 1.2 | 2.5 | 5.0 | 7.5 |
| | Kernel Weight | 120 | 120 | 150 | 300 | 600 | 900 |
| | | FILM COAT: | | | | | |
| 6 | Hydroxypropyl Methylcellulose 6 cps-2910 | 1.6 | 1.6 | 2.0 | 4.0 | 8.0 | 12.0 |
| 7 | Talc | 1.2 | 1.2 | 1.5 | 3.0 | 6.0 | 9.0 |
| 8 | Titanium Dioxide | 1.2 | 1.2 | 1.5 | 3.0 | 6.0 | 9.0 |
| | Total Tablet Weight | 124 | 124 | 155 | 310 | 620 | 930 |

Manufacturing Procedure:
1. Mix Items 1, 2 and 3 in a suitable mixer for 15 minutes.
2. Granulate the powder mix from Step 1 with 15% Povidone K30 Solution (Item 4).
3. Dry the granulation from Step 2 at 50° C.
4. Pass the granulation from Step 3 through a suitable milling equipment
5. Add the Item 5 to the milled granulation Step 4 and mix for 5 minutes.
6. Compress the granulation from Step 5 on a suitable press.
7. Using a suitable air spray system, coat the kernels from Step 6 with a Film Coat Suspension containing Hydroxypropyl Methylcellulose 6 cps-2910, Talc and Titanium Dioxide.

EXAMPLE 8

| | CAPSULE FORMULATION | | | | | |
|---|---|---|---|---|---|---|
| | | | | mg/Capsule | | |
| Item | Ingredients | 5 mg | 25 mg | 100 mg | 250 mg | 500 mg |
| 1 | Compound of formula I | 5 | 25 | 100 | 250 | 500 |
| 2 | Hydrous Lactose | 159 | 123 | 148 | 50 | 75 |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 350 | 675 |

Manufacturing Procedure:
1. Mix Items 1, 2 and 3 in a suitable mixer for 15 minutes.
2. Add Items 4 & 5 and mix for 3 minutes.
3. Fill the powder mix from Step 2 into a suitable capsule.

What is claimed is:

1. A compound of formula I

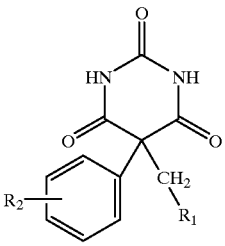

wherein $R_1$ is hydrogen, C1–C13 alkyl, C1–C13 alkyl substituted by one or more substituents selected from hydroxy, halogen or aryl, C2–C13 alkenyl, C2–C13 alkenyl substituted by one or more substituents selected from hydroxy, halogen or aryl, C2–C13 alkynyl, C2–C13 alkynyl substituted by one or more substituents selected from hydroxy, halogen or aryl, C1–C11 alkoxy, C1–C11 alkoxy substituted by one or more substituents selected from hydroxy, halogen or aryl; aryloxy or alkoxyalkyl, and $R_2$ is aryloxy, or a pharmaceutically acceptable salt of an acidic compound of formula I wherein aryl, alone or in combination, means phenyl which is unsubstituted or substituted by one or more substitutents selected from C1–C13 alkyl, hydroxy, C1–C11 alkoxy or halogen.

2. A compound of claim 1, wherein $R_2$ is in the para position.

3. A compound of claim 2, wherein $R_2$ is phenoxy.

4. A compound of claim 3, wherein R1 is hydrogen, C1–C13 alkyl, C1–C13 alkyl substituted by one or more substituents selected from hydroxy, halogen or aryl, or C1–C11 alkoxy.

5. A compound of claim 3, wherein R1 is C1–C11 alkoxy substituted by one or more substituents selected from hydroxy, halogen or aryl; or alkylalkoxy.

6. A compound of claim 5, wherein $R_1$ is benzyloxy.

7. The compound of claim 4, 5-methyl-5-(4-phenoxyphenyl) pyrimidine-2,4,6-trione.

8. A compound of claim 4, wherein R1 is C1–C13 alkyl.

9. The compound of claim 8, 5-hexyl-5-(4-phenoxyphenyl) pyrimidine-2,4,6-trione.

10. The compound of claim 6, 5-benzyloxymethyl-5-(4-phenoxyphenyl)pyrimidine-2,4,6-trione.

11. The compound of claim 4, wherein R1 is C1–C13 alkyl substituted by one or more substituents selected from hydroxy, halogen or aryl.

12. The compound of claim 8, 5-(2-hydroxyethyl)-5-(4-phenoxyphenyl)pyrimidine-2,4,6-trione.

* * * * *

UNITED STATES PATENT AND TRADEMARK OFFICE
CERTIFICATE OF CORRECTION

PATENT NO.    : 6,265,578 B1
DATED         : July 24, 2001
INVENTOR(S)   : Louise Helen Foley, Robert Edward Palermo, and Ping Wang Page 1 of 1

It is certified that error appears in the above-identified patent and that said Letters Patent is hereby corrected as shown below:

Column 12, claim 1,
Line 32, delete "$R_2$ is aryloxy, or a pharmaceutically acceptable salt of an" and replace with the following:
-- $R_2$ is aryloxy, or
   a pharmaceutically acceptable salt of an --

Column 12, claim 4,
Line 41, delete "R1" and insert -- $R_1$ --

Column 12, claim 5,
Line 45, delete "R1" and insert -- $R_1$ --
Line 47, delete "alkylalkoxy" and insert -- alkoxyalkyl --

Column 12, claim 8,
Line 51, delete "R1" and insert -- $R_1$ --

Column 12, claim 11,
Line 57, delete "R1" and insert -- $R_1$ --

Signed and Sealed this

Ninth Day of April, 2002

Attest:

*Attesting Officer*

JAMES E. ROGAN
*Director of the United States Patent and Trademark Office*